(12) United States Patent
Eun et al.

(10) Patent No.: US 10,302,412 B2
(45) Date of Patent: May 28, 2019

(54) TESTING APPARATUS AND MANUFACTURING APPARATUS FOR TESTING LIGHT EMITTING DEVICE PACKAGE

(71) Applicant: SAMSUNG ELECTRONICS CO., LTD., Suwon-si (KR)

(72) Inventors: Young Hyo Eun, Asan-si (KR); Ju Hyun Song, Cheonan-si (KR); Jae Sung Kim, Yongin-si (KR); Tae Hee Song, Gunpo-si (KR); Shin Min Rhee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 253 days.

(21) Appl. No.: 15/343,733

(22) Filed: Nov. 4, 2016

(65) Prior Publication Data
US 2017/0261310 A1 Sep. 14, 2017

(30) Foreign Application Priority Data
Mar. 11, 2016 (KR) ........................ 10-2016-0029636

(51) Int. Cl.
*G01B 11/00* (2006.01)
*G01J 3/50* (2006.01)
*G01N 21/25* (2006.01)
*G01J 3/46* (2006.01)
*G01N 21/95* (2006.01)

(52) U.S. Cl.
CPC .............. *G01B 11/002* (2013.01); *G01J 3/50* (2013.01); *G01J 3/505* (2013.01); *G01N 21/253* (2013.01); *G01J 3/462* (2013.01); *G01N 2021/9511* (2013.01); *H01L 2224/48091* (2013.01); *H01L 2224/48247* (2013.01); *H01L 2224/49107* (2013.01); *H01L 2924/181* (2013.01)

(58) Field of Classification Search
CPC ... G01J 3/505; G01J 3/462; G01J 3/50; H01L 2224/48091; H01L 2924/181; H01L 2224/48247; H01L 2224/49107; H01L 33/62; G01B 11/002; G01N 2021/9511; G01N 21/253
See application file for complete search history.

(56) References Cited
U.S. PATENT DOCUMENTS 6,372,608 B1   4/2002  Shimoda et al.
6,645,830 B2  11/2003  Shimoda et al.
(Continued)

FOREIGN PATENT DOCUMENTS

KR  10-2010-0054623 A  5/2010
KR  10-2011-0007705 A  1/2011
(Continued)

*Primary Examiner* — Hina F Ayub
*Assistant Examiner* — Amanda Merlino
(74) *Attorney, Agent, or Firm* — Sughrue Mion, PLLC

(57) ABSTRACT

An apparatus includes a lighting unit configured to irradiate a light emitting device package including a light transmitting resin containing a light conversion material with light having a certain color; a camera configured to capture an image of the light emitting device package; and a controller configured to determine color coordinates of the light emitting device package using the image, captured by the camera, to determine whether the light emitting device package is defective.

21 Claims, 22 Drawing Sheets

(56) References Cited

U.S. PATENT DOCUMENTS

| | | |
|---|---|---|
| RE38,466 E | 3/2004 | Inoue et al. |
| 6,818,465 B2 | 11/2004 | Biwa et al. |
| 6,818,530 B2 | 11/2004 | Shimoda et al. |
| 6,858,081 B2 | 2/2005 | Biwa et al. |
| 6,967,353 B2 | 11/2005 | Suzuki et al. |
| 7,002,182 B2 | 2/2006 | Okuyama et al. |
| 7,053,397 B1 | 5/2006 | Nishioka |
| 7,084,420 B2 | 8/2006 | Kim et al. |
| 7,087,932 B2 | 8/2006 | Okuyama et al. |
| 7,154,124 B2 | 12/2006 | Han et al. |
| 7,208,725 B2 | 4/2007 | Sherrer et al. |
| 7,288,758 B2 | 10/2007 | Sherrer et al. |
| 7,319,044 B2 | 1/2008 | Han et al. |
| 7,501,656 B2 | 3/2009 | Han et al. |
| 7,709,857 B2 | 5/2010 | Kim et al. |
| 7,759,140 B2 | 7/2010 | Lee et al. |
| 7,781,727 B2 | 8/2010 | Sherrer et al. |
| 7,790,482 B2 | 9/2010 | Han et al. |
| 7,940,350 B2 | 5/2011 | Jeong |
| 7,959,312 B2 | 6/2011 | Yoo et al. |
| 7,964,881 B2 | 6/2011 | Choi et al. |
| 7,985,976 B2 | 7/2011 | Choi et al. |
| 7,994,525 B2 | 8/2011 | Lee et al. |
| 8,008,683 B2 | 8/2011 | Choi et al. |
| 8,013,352 B2 | 9/2011 | Lee et al. |
| 8,049,161 B2 | 11/2011 | Sherrer et al. |
| 8,129,711 B2 | 3/2012 | Kang et al. |
| 8,179,938 B2 | 5/2012 | Kim |
| 8,227,274 B2 | 7/2012 | Cho |
| 8,263,987 B2 | 9/2012 | Choi et al. |
| 8,324,646 B2 | 12/2012 | Lee et al. |
| 8,399,944 B2 | 3/2013 | Kwak et al. |
| 8,432,511 B2 | 4/2013 | Jeong |
| 8,459,832 B2 | 6/2013 | Kim |
| 8,502,242 B2 | 8/2013 | Kim |
| 8,536,604 B2 | 9/2013 | Kwak et al. |
| 8,735,931 B2 | 5/2014 | Han et al. |
| 8,766,295 B2 | 7/2014 | Kim |
| 9,132,629 B2 | 9/2015 | Ward et al. |
| 2012/0105836 A1* | 5/2012 | Yoon .................... G01J 3/0267 356/244 |

FOREIGN PATENT DOCUMENTS

| | | |
|---|---|---|
| KR | 10-2012-0128464 A | 11/2012 |
| KR | 10-2013-0130567 A | 12/2013 |
| KR | 10-1528349 B1 | 6/2015 |

* cited by examiner

TESTING APPARATUS AND MANUFACTURING APPARATUS FOR TESTING LIGHT EMITTING DEVICE PACKAGE

CROSS-REFERENCE TO RELATED APPLICATION

This application claims priority from Korean Patent Application No. 10-2016-0029636, filed on Mar. 11, 2016 in the Korean Intellectual Property Office, the disclosure of which is incorporated herein by reference in its entirety.

BACKGROUND

1. Field

Apparatuses consistent with example embodiments relate to a testing apparatus and a manufacturing apparatus for manufacturing a light emitting device package.

2. Description of Related Art

Light emitting diodes (LEDs) have many advantages, such as relatively low power consumption, a relatively long lifespan, and the ability to generate light having various colors, as compared to conventional light sources, such as fluorescent lamps and incandescent lamps. Based on such advantages, LEDs are being applied to be used in devices within a wide range of fields, such as in various types of lighting devices, the backlight units of display devices, and vehicle headlamps. The LEDs may be mounted in light emitting device packages, and light emitting device packages may include light transmitting resins containing light conversion materials in order to adjust colors of light and protect LEDs.

However, when the amount of resin is not properly controlled, the LED packages may not emit desired colors of light. The related art detectors for detecting the amount of resin are high-priced devices which are difficult to apply on the production line.

Thus, there is a need for affordable and versatile device capable of quickly detecting defects in the light emitting device package.

SUMMARY

Example embodiments may provide a testing apparatus and a manufacturing apparatus for manufacturing a light emitting device package, which may effectively determine whether a proper amount of a light transmitting resin has been dispensed in a process of dispensing the light transmitting resin containing a light conversion material.

According to an aspect of an example embodiment, an apparatus for testing a light emitting device package may include a lighting unit configured to irradiate a light emitting device package including a light transmitting resin containing a light conversion material with light having a certain color, a camera configured to capture an image of the light emitting device package above the light transmitting resin, and a controller configured to calculate color coordinates of the light emitting device package using the image, captured by the camera, to determine whether the light emitting device package is defective.

According to an aspect of another example embodiment, an apparatus for manufacturing a light emitting device package may include a resin dispenser configured to dispense a light transmitting resin containing a light conversion material onto the light emitting device package in dot units, and a testing device configured to irradiate the light emitting device package, onto which the light transmitting resin has been dispensed, with light having a certain color to obtain an image of the light emitting device package, calculate color coordinates based on a certain color coordinate system using the obtained image, and compare a reference region, defined in the color coordinate system, to the calculated color coordinates to determine whether the dispensed amount of the light transmitting resin is defective.

According to an aspect of another example embodiment, an apparatus may include a lighting unit configured to emit light onto a light emitting diode (LED) disposed in a cavity of a light emitting device package, the cavity being filled with a resin containing a light conversion material; a camera configured to capture an image of a top of the resin disposed on the LED; and a processor configured to calculate color coordinates of the light conversion material dispersed in the resin from the captured image, and determine whether the light emitting device package is defective based on the calculated color coordinates.

BRIEF DESCRIPTION OF DRAWINGS

The above and/or other aspects will be more apparent by describing certain example embodiments with reference to the accompanying drawings, in which.

DETAILED DESCRIPTION

Figure 1:
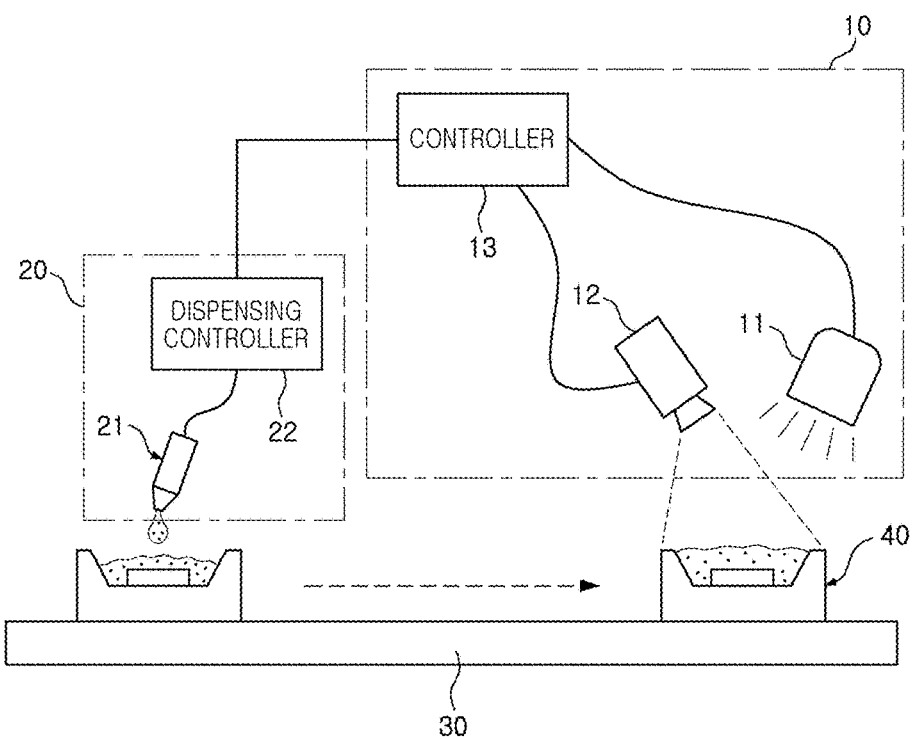
FIG. 1 is a schematic diagram of a manufacturing apparatus for manufacturing a light emitting device package according to an example embodiment.

FIG. 1 is a schematic diagram of a manufacturing apparatus for manufacturing a light emitting device package according to an example embodiment.

Referring first to FIG. 1, a manufacturing apparatus 1 for manufacturing a light emitting device package according to an example embodiment may include a resin dispenser 20 dispensing a light transmitting resin onto a light emitting device package or packages 40 and a jig 30 on which the light emitting device package 40 may be seated. A light transmitting resin dispensed onto the light emitting device package 40 may include a light conversion material adjusting colors of light output by a light emitting device. The resin dispenser 20 may include a dispenser 21 dispensing a light transmitting resin in dot units and a dispensing controller 22.

After the light transmitting resin has been dispensed, a testing apparatus 10 may determine whether the light transmitting resin has been properly dispensed. The testing apparatus 10 may irradiate the light emitting device package 40 with light using a lighting unit 11, and may obtain an image of the light emitting device package 40 using a camera 12. The lighting unit 11 and the camera 12 are illustrated as separate components as an example. However, the camera 11 and the lighting unit 12 may be a single integrated component, e.g., the camera itself may provide light. The lighting unit 11 may have a light source emitting light having a certain color, and as an example, may include a blue LED or an ultraviolet (UV) LED as a light source. A color of light emitted by the lighting unit 11 may be substantially the same as that of light emitted by a light emitting device included in the light emitting device package 40.

The camera 12 may capture an image of the light emitting device package 40. The image captured by the camera 12 may be an image obtained by imaging an upper surface of the light emitting device package 40 coated with a light transmitting resin containing a light conversion material. A controller 13, e.g., a processor or a microprocessor, may control operations of the lighting unit 11 and the camera 12, and may calculate color coordinates using the image captured by the camera 12. The controller 13 may determine whether a proper amount of a light transmitting resin has been dispensed based on the calculated color coordinates.

In an example embodiment, the controller 13 may determine whether an amount of a light transmitting resin dispensed by the dispenser 21 in dot units, a dotting amount, is proper. The controller 13 may determine that the dotting amount has not been properly controlled when the color coordinates calculated using the image captured by the camera 12 are outside of a certain reference region. The reference region may include color coordinates calculated using light actually emitted by the light emitting device package 40 when the light emitting device package 40 includes proper amounts of a light transmitting resin and a light conversion material.

In an example embodiment, the testing apparatus 10 and the resin dispenser 20 may be provided as a single device. For example, the testing apparatus 10 may be combined with a device for a process of dispensing a light transmitting resin onto the light emitting device package 40 so that the testing apparatus 10 and the resin dispenser 20 may be provided as one device. The controller 13 and the dispensing controller 22 may be integral as a single control module.

Figure 2:
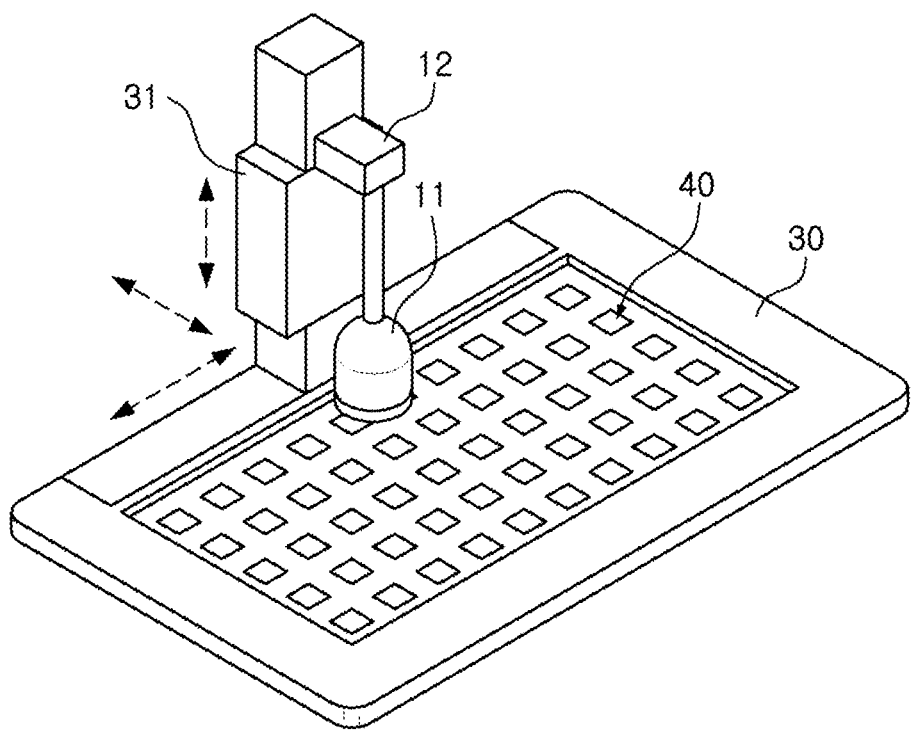
FIG. 2 is a perspective view illustrating the exterior of a testing apparatus for testing a light emitting device package according to an example embodiment.

FIG. 2 is a perspective view illustrating the exterior of a testing apparatus for testing a light emitting device package according to an example embodiment.

Referring to FIG. 2, a testing apparatus 10 according to an example embodiment may include a lighting unit 11 and a camera 12. The controller 13 may be mounted in a housing of the testing apparatus 10 so as not to be exposed. Light emitting device packages 40 may be disposed in a plurality of rows and columns to be aligned within the jig. The lighting unit 11 and the camera 12 may be coupled to a support portion 31 to move from top to bottom, or left to right via driving mechanisms, e.g., a motor and a gear, disposed at the support portion 31. The lighting unit 11 and the camera 12 may inspect the respective light emitting device packages 40 while moving in the rows and columns in which the light emitting device packages 40 are arranged.

The lighting unit 11 may include a light source emitting light having a certain color, and may simultaneously irradiate two or more of the light emitting device packages 40 adjacent to each other with light. The camera 12 may capture an image of the light emitting device package 40 irradiated by the lighting unit 11, and the image may be analyzed by the controller 13 to be used as data for determining whether the light emitting device package 40 is defective.

The controller 13 may set a test region in the image of the light emitting device package 40, and may calculate an average of respective red, green, and blue (RGB) values of pixels included in the set test region. The test region may include a region onto which a light transmitting resin has been dispensed, and may be a region in which a light conversion material is present. The controller 13 may calculate color coordinates defined in a certain color coordinate system using the average of the respective RGB values. The color coordinate system may be at least one among CIELAB, CIELUV, CIELCh, and Yxy color coordinate systems.

The controller 13 may set a certain reference region in the color coordinate system, and may determine whether the color coordinate calculated using the average of the respective RGB values is outside of the reference region to determine whether a light transmitting resin is properly dispensed onto the light emitting device package 40. When an excessive or insufficient amount of a light transmitting resin has been dispensed, as an amount of a light conversion material included in the light emitting device package 40 changes, the average of the respective RGB values of the image captured by the camera 12 may change. The controller 13 may determine that an excessive or insufficient amount of a light transmitting resin has been dispensed when the color coordinates calculated on the basis of the average of the respective RGB values of the image are outside of the reference region.

In an example embodiment, the camera 12 may capture a single image of two images of the light emitting device packages 40 adjacent to each other in top and bottom, or right and left directions. The two light emitting device packages 40 included in the single image may receive light having different intensities from the lighting unit 11. The controller 13 may calculate color coordinates from each of the two light emitting device packages 40 included in the single image. The controller 13 may separately determine whether light transmitting resins disposed onto the respective light emitting device packages 40 are defective by comparing color coordinates calculated from the respective light emitting device packages 40 to different reference regions.

Figure 3:
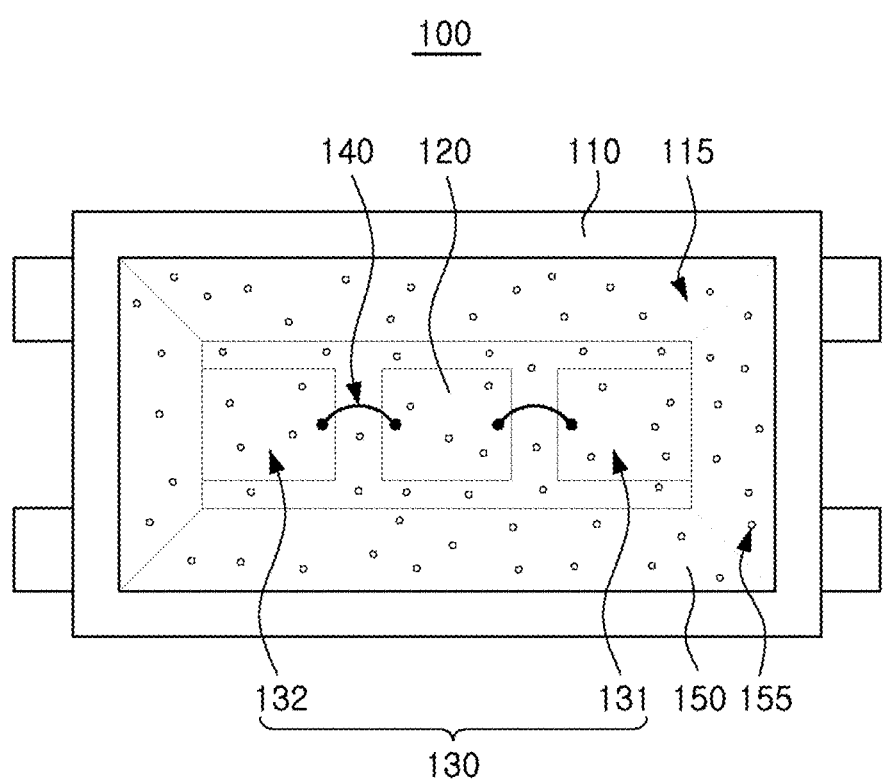
FIG. 3 is a plan view of a light emitting device package that may be manufactured using a manufacturing apparatus for manufacturing a light emitting device package according to an example embodiment.
Figure 4:
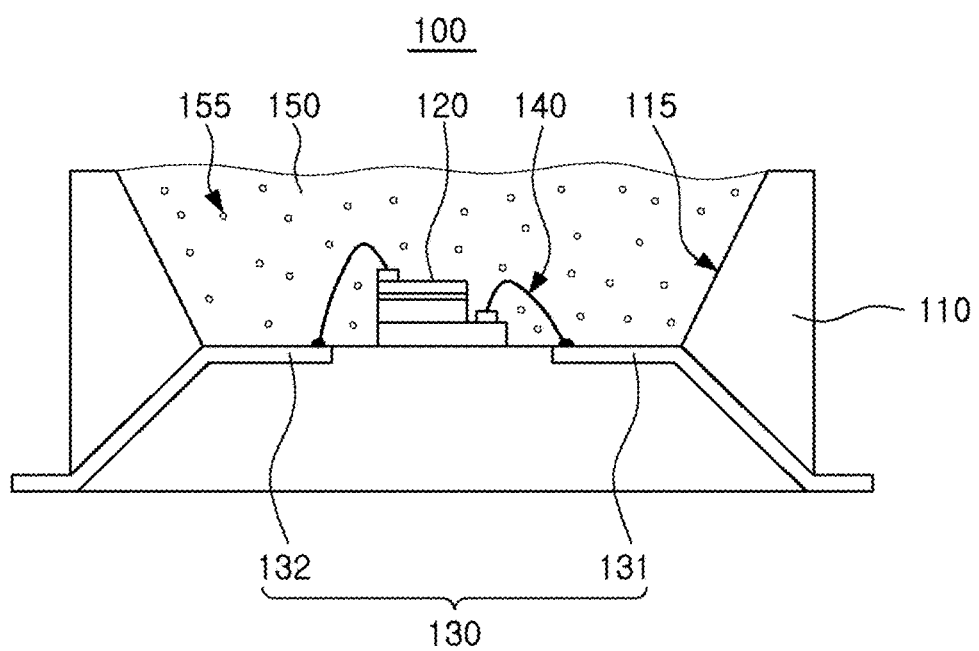
FIG. 4 is a cross-sectional view of the light emitting device package that may be manufactured by the manufacturing apparatus for manufacturing the light emitting device package according to an example embodiment.

FIG. 3 is a plan view of a light emitting device package that may be manufactured using a manufacturing apparatus for manufacturing a light emitting device package according to an example embodiment. FIG. 4 is a cross-sectional view of the light emitting device package that may be manufactured by the manufacturing apparatus for manufacturing the light emitting device package according to an example embodiment.

Referring to FIGS. 3 and 4, a light emitting device package 100 according to an example embodiment may include a package body 110 providing a mounting space 115, a light emitting element 120 disposed in the mounting space 115, and a lead frame 130 for supplying an electrical signal to the light emitting element 120. The lead frame 130 may include a first lead frame 131 and a second lead frame 132, and the light emitting element 120 and each of the first and second lead frames 131 and 132 may be electrically connected to each other by a wire 140. Alternatively, unlike an example embodiment illustrated in FIGS. 3 and 4, the light emitting element 120 may be electrically connected to the first and second lead frames 131 and 132 by a flip-chip bonding.

A portion of the lead frame 130 may protrude externally from the package body 110 to receive an electrical signal. A portion of the lead frame 130 may also be exposed in the mounting space 115 to be connected to an electrode of the light emitting element 120 by the wire 140 or by the flip-chip bonding. The light emitting element 120 may be disposed in the mounting space 115, and may then be connected to the lead frame 130. The mounting space 115 may be filled with a light transmitting resin 150 including a light conversion material 155.

The light conversion material 155 may be a material emitting light having a different wavelength by receiving light emitted by the light emitting element 120, such as a phosphor or quantum dots. As a material having excellent light transmittance, the light transmitting resin 150 may be dispensed while containing the light conversion material 155 to fill the mounting space 115. The light transmitting resin 150 may also protect the light emitting element 120, the lead frame 130, the wire 140, or the like, exposed in the mounting space 115.

For example, the light emitting element 120 emitting blue light may be prepared in the mounting space 115, and the light conversion material 155 emitting yellow light by being excited by the blue light may be included in the light transmitting resin 150, so that the light emitting device package 100 emitting white light may be implemented. When an excessive or insufficient amount of the light transmitting resin 150 has been dispensed, the light emitting device package 100 may not emit light having a desired color. Thus, an apparatus determining whether a proper amount of the light transmitting resin 150 has been dispensed onto the light emitting device package 100 may be required.

As described above with reference to FIGS. 1 and 2, the testing apparatus 10 according to an example embodiment may include the lighting unit 11 irradiating the light emitting device package 100 with light having a certain color, the camera 12 capturing an image of the light emitting device package 100, and the controller 13. The testing apparatus 10 may be implemented as a single device with an apparatus for dispensing the light transmitting resin 150. Thus, the light transmitting resin 150 may be dispensed onto the light emitting device package 100, and a dispensed amount of the dispensed light transmitting resin 150 may be inspected, so that whether the dispensed amount of the light transmitting resin 150 and a dispensed amount of the light conversion material 155 are proper can be detected in a self-process.

The light emitting device package 100 according to an example embodiment illustrated in FIGS. 3 and 4 may be manufactured by the manufacturing apparatus 1 illustrated in FIG. 1. In an example embodiment, the manufacturing apparatus 1 may dispense the light transmitting resin 150 containing the light conversion material 155 into the mounting space 115 of the package body 110 using the dispenser 21. The light transmitting resin 150 may be dispensed by the dispenser 21 in dot units, and the manufacturing apparatus 1 may determine whether a dotting height of the light transmitting resin 150 dispensed by the dispenser 21 is properly controlled using the testing apparatus 10.

Figure 5:
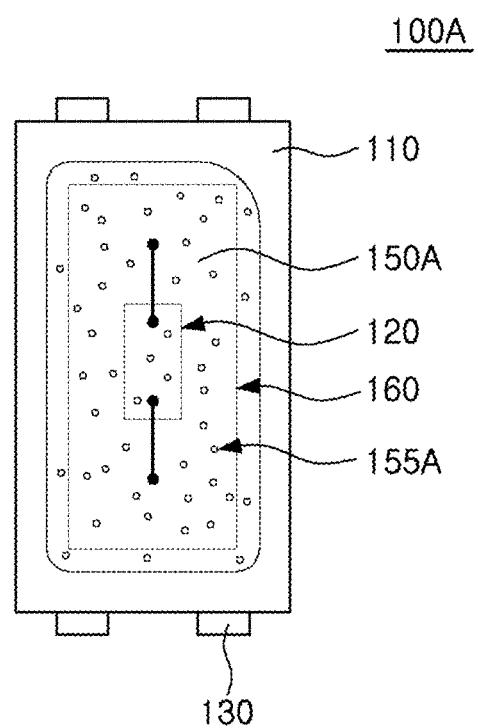
FIGS. 5, 6, and 7 are images of light emitting device packages captured by a testing apparatus for testing a light emitting device package according to an example embodiment.
Figure 6:
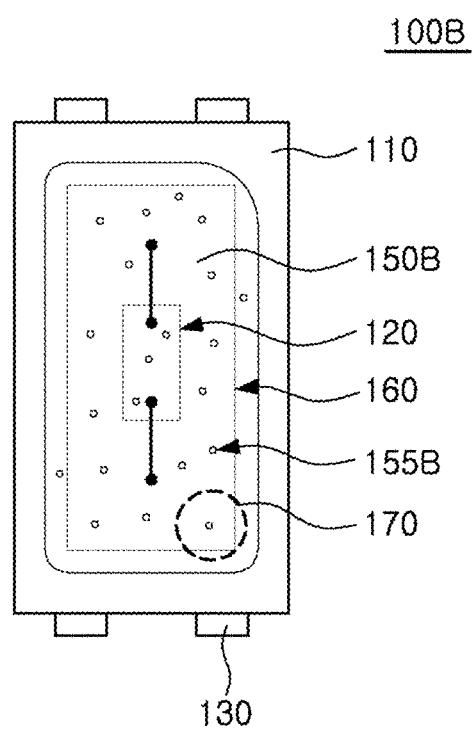
Figure 7:
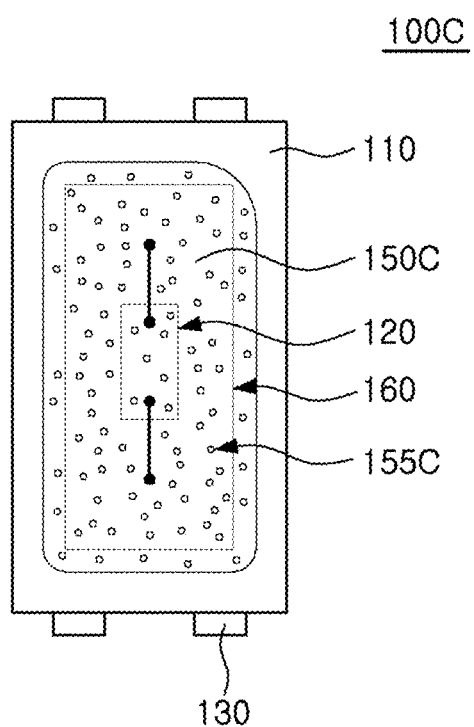

FIGS. 5, 6, and 7 are images of light emitting device packages captured by a testing apparatus for testing a light emitting device package according to an example embodiment.

In example embodiments of FIGS. 5 through 7, each of light emitting device packages 100A, 100B, and 100C may include a blue LED as a light emitting element 120, and the light emitting device packages 100A, 100B, and 100C may include light conversion materials 155A, 155B, and 155C, respectively, each of which receives blue light to emit yellow excitation light. The testing apparatus 10 may include the lighting unit 11 emitting light having the same color as that emitted by the light emitting element 120. For example, an image according to an example embodiment illustrated in FIGS. 5 through 7 may be captured by the camera 12 while the lighting unit 11 emits blue light. When the light emitting element 120 includes a UV LED, the lighting unit 11 may include a light source that emits light in a UV wavelength band.

FIG. 5 may be an image of the light emitting device package 100A onto which a proper amount of the light transmitting resin 150A has been dispensed. FIGS. 6 and 7 may be images of the light emitting device packages 100B and 100C onto which abnormal amounts of light transmitting resins 150B and 150C are dispensed. Referring to FIGS. 5 through 7, each of the images of the light emitting device packages 100A, 100B, and 100C captured by the camera 12 may display a package body 110, the light emitting element 120, a lead frame 130, or the like, and may also display the light transmitting resins 150A, 150B, and 150C and the light conversion materials 155A, 155B, and 155C included therein. The light emitting device package 100B may include the light conversion material 155B in an amount smaller than that of the light conversion material 155A included in the light emitting device package 100A, and the light emitting device package 100C may include the light conversion material 155C in an amount greater than that of the light conversion material 155A included in the light emitting device package 100A.

When the camera 12 captures the images of the light emitting device packages 100A, 100B, and 100C, the controller 13 may set a certain test region 160 in each of the images. The test region 160 may be a region in which the light conversion materials 155A, 155B, and 155C may be intensely distributed when viewed from above. Referring to FIGS. 5 through 7, the test region 160 may be applied to each of the light emitting device packages 100A, 100B, and 100C in the same manner.

The controller 13 may calculate an average of RGB values of pixels included in the test region 160. The image may include a plurality of pixels, and each of the pixels may have an RGB value. The controller 13 may calculate an average of RGB values of pixels included in the test region 160, and may produce color coordinate values of the test region 160 using the calculated average.

The color coordinate values of the test region 160 may be calculated using the average according to various formulae known in the related art. In an example embodiment, the controller 13 may calculate color coordinate values, based on an XYZ color coordinate system, using an average of RGB values of pixels included in the test region 160. The controller 13 may convert the color coordinate values based on the XYZ color coordinate system to color coordinate values based on other color coordinate systems, such as a Yxy color coordinate system, a CIELAB color coordinate system, and a CIELUV color coordinate system.

The controller 13 may compare the converted color coordinate values to a certain reference region to determine whether the light emitting device packages 100A, 100B, and 100C are defective. When the images illustrated in FIGS. 5 through 7 are compared, the light emitting device package 100B may include a relatively small amount of the light conversion material 155B in the test region 160, and may also have an abnormal region 170 in which the light conversion material 155B is barely present. The light emitting device package 100C may include a relatively large amount of the light conversion material 155C in the test region 160. A difference between contents of light conversion materials 155B and 155C may cause color coordinate values, calculated in the test region 160 of each of the images of FIGS. 5 through 7, to be different from each other. The color coordinate values will hereinafter be described with reference to FIGS. 8 and 9.

Figure 8:
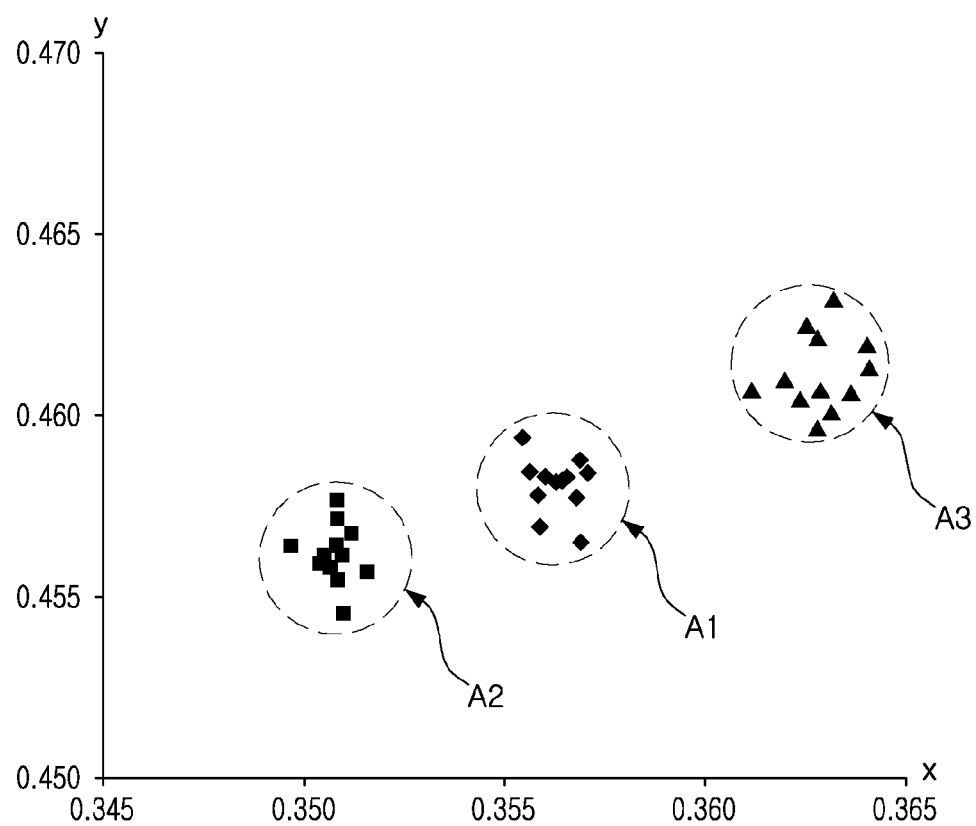
FIGS. 8 and 9 are graphs of color coordinate values calculated by a testing apparatus for testing a light emitting device package according to an example embodiment.
Figure 9:
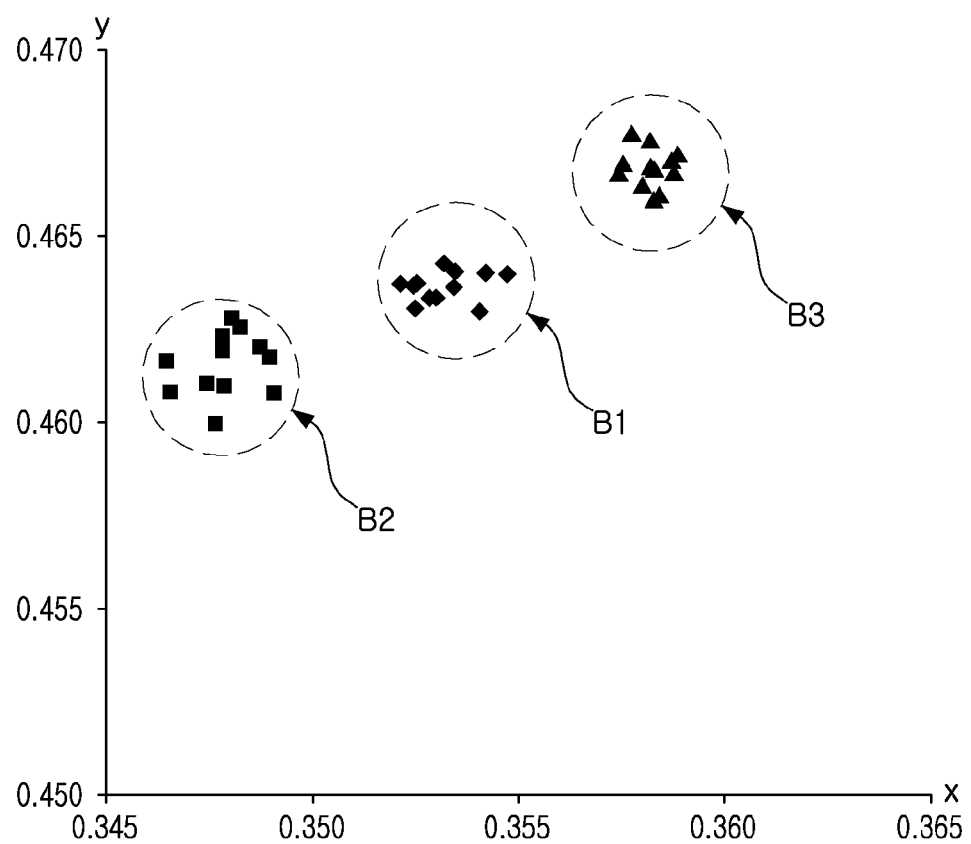

FIGS. 8 and 9 are graphs of color coordinate values calculated by a testing apparatus for testing a light emitting device package according to an example embodiment.

FIGS. 8 and 9 may all be graphs based on the Yxy color coordinate system. In contrast, a graph based on other color coordinate systems may also be applied. Referring to FIGS. 8 and 9, color coordinate values calculated by the testing apparatus 10 according to an example embodiment may be different from each other according to amounts of the light transmitting resins 150A, 150B, and 150C and the light conversion materials 155A, 155B, and 155C included therein. In an example embodiment, the amounts of the light transmitting resins 150A, 150B, and 150C and the light conversion materials 155A, 155B, and 155C may be determined according to dotting amounts in which the light transmitting resins 150A, 150B, and 150C and the light conversion materials 155A, 155B, and 155C are dispensed.

Referring first to FIG. 8, color coordinate values generated by the controller 13 using the light emitting device package 100A may be included in region A1. When the color coordinate values are included in region A1, the controller 13 may determine that the light emitting device package 100A includes proper amounts of the light transmitting resin 150A and the light conversion material 155A. For example, when the color coordinate values are included in region A1, the controller 13 may determine that the light emitting device package 100A is a good product.

Color coordinate values generated by the controller 13 using the light emitting device package 100B may be included in region A2. As noted above, the light emitting device package 100B may have the light conversion material 155B in an amount smaller than that of the light conversion material 155A included in the light emitting device package 100A. For example, when the dispenser 21 dispenses the light transmitting resin 150B in a dotting amount smaller than that within a normal range, the light emitting device package 100B may be manufactured.

Color coordinate values generated by the controller 13 using the light emitting device package 100C may be included in region A3. As illustrated in an example embodiment of FIG. 7, the light emitting device package 100C may have the light conversion material 155C in an amount greater than that of the light conversion material 155A included in the light emitting device package 100A. For example, when the dispenser 21 dispenses the light transmitting resin 150C in a dotting amount greater than that within the normal range, the light emitting device package 100C may be manufactured.

When the light emitting element 120 includes a blue LED and the light conversion material 155C emits yellow excitation light by being excited by blue light, a blue component may be stronger in the image obtained by imaging the light emitting device package 100B, and a yellow component may be stronger in the image obtained by imaging the light emitting device package 100C. Thus, color coordinate values calculated using the image of the light emitting device package 100B may have x and y values smaller than color coordinate values calculated using the image of the light emitting device package 100A. In contrast, color coordinate values calculated using the image of the light emitting device package 100C may have x and y values greater than color coordinate values calculated using the image of the light emitting device package 100A.

For example, the color coordinate values calculated using the image of the light emitting device package 100B may be located in region A2 in the Yxy color coordinate system illustrated in FIG. 8. The color coordinate values calculated using the image of the light emitting device package 100C may be located in region A3 in the Yxy color coordinate system illustrated in FIG. 8. Thus, the controller 13 may compare the x and y values of the color coordinate values, calculated using the images of the light emitting device packages 100A, 100B, and 100C, to x and y values of a reference region, for example, region A1 to determine whether the amounts of light conversion materials 155A, 155B, and 155C are excessive or insufficient.

The graph illustrated in FIG. 9 may be a graph of color coordinate values calculated using the images of the light emitting device packages 100A, 100B, and 100C that may be obtained using a lighting unit 11 having a relatively lower output than that of the example embodiment illustrated in FIG. 8. In the case that each of the light emitting device packages 100A, 100B, and 100C includes a blue LED as the light emitting element 120 and the lighting unit 11 also emits blue light, color coordinate values calculated using identical light emitting device packages 100A, 100B, and 100C may have a smaller x value and a greater y value depending on a decrease in optical power of the lighting unit 11. Here, the case in which the Yxy color coordinate system is adapted is taken as an example, and when the Yxy color coordinate system is changed, a movement trend of color coordinate values may be changed.

For example, when the light emitting device package 100A is irradiated with light emitted by the lighting unit 11 having relatively weak optical power and then color coordinate values are calculated, color coordinate values included in region B1 of the graph illustrated in FIG. 9 may be obtained. Similarly, when the light emitting device packages 100B and 100C are irradiated with light emitted by the lighting unit 11 having relatively weak optical power and then color coordinate values are calculated, color coordinate values included in region B2 and region B3 of the graph illustrated in FIG. 9 may be obtained. Thus, the controller 13 may set reference regions, such as regions A1 and B1, compared to color coordinate values, to be different from each other, based on optical power of the lighting unit 11.

Figure 10A:
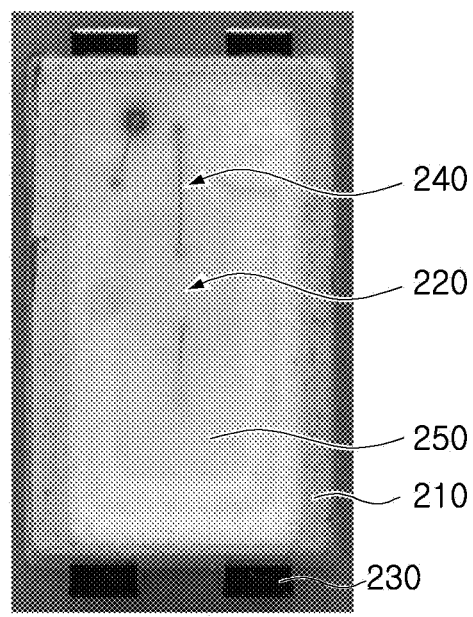
FIGS. 10A, 10B, and 10C are images of light emitting device packages generated by a testing apparatus for testing a light emitting device package according to an example embodiment.
Figure 10B:
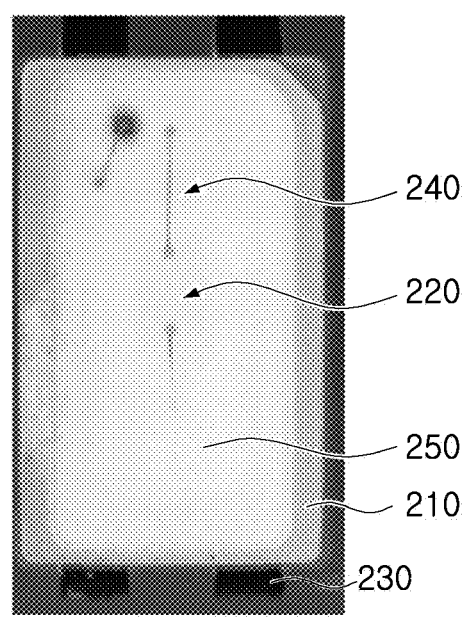
Figure 10C:
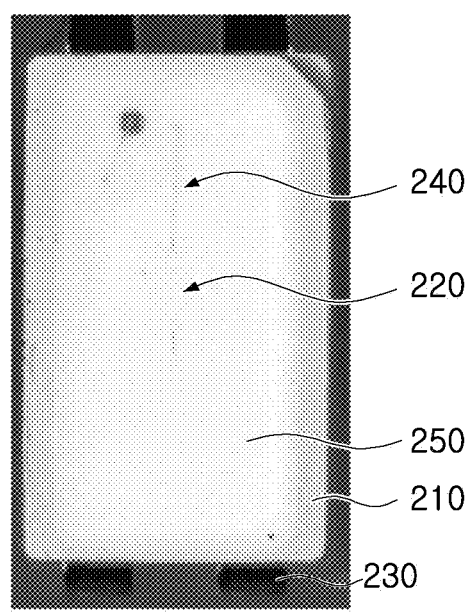
Figure 11:
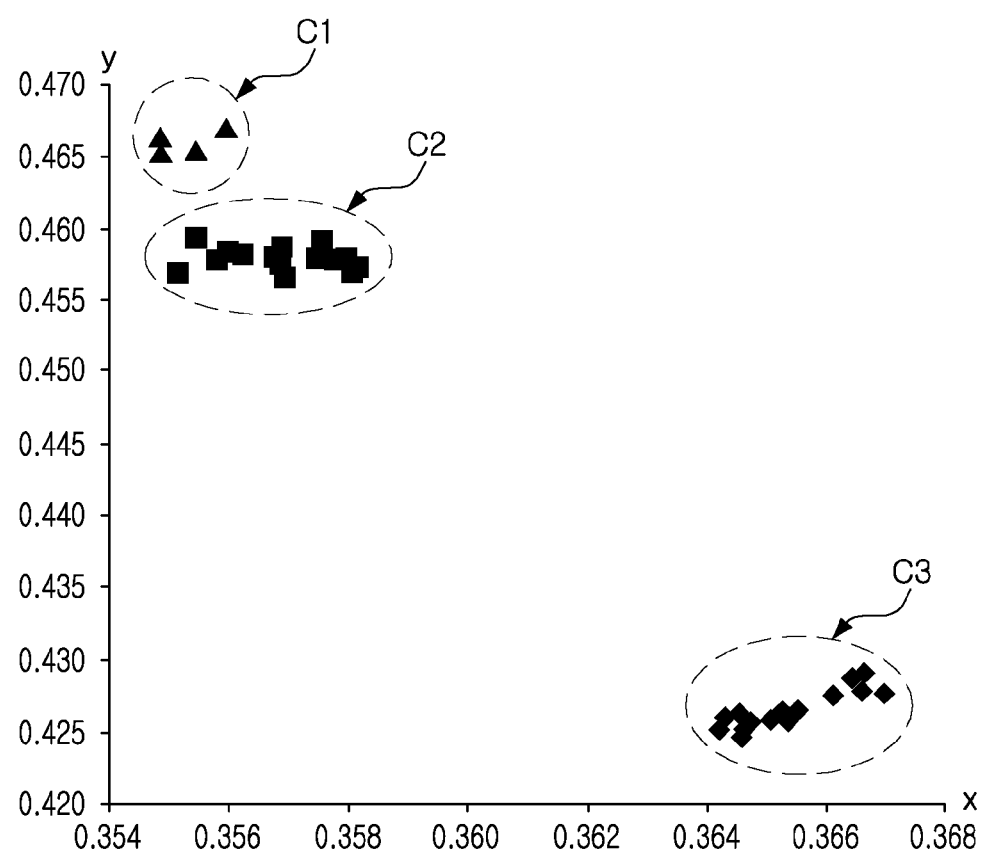
FIG. 11 is a graph of color coordinate values that may be calculated using the images illustrated in FIGS. 10A through 10C.

FIGS. 10A, 10B, and 10C are images of light emitting device packages generated by a testing apparatus for testing a light emitting device package according to an example embodiment. FIG. 11 is a graph of color coordinate values that may be calculated using the images illustrated in FIGS. 10A through 10C.

Referring to FIGS. 10A through 10C, a light emitting device package 200 may include a package body 210, a light emitting element 220, a lead frame 230, a wire 240, and a light transmitting resin 250. Images 200A, 200B, and 200C illustrated in FIGS. 10A through 10C may all be obtained by imaging an identical light emitting device package 200, and may be captured while the lighting unit 11 irradiates light having different levels of intensity. In an example embodiment, the image 200A may be captured while light having a lower intensity than that of light irradiated to the images 200B and 200C is irradiated, and the image 200C may be captured while light having a higher intensity than that of light irradiated to the images 200A and 200B is irradiated. Alternatively, the image 200A may be captured with light irradiated for a shortest period of time, and the image 200C may be captured with light irradiated for a longest period of time.

Referring to FIG. 11, color coordinate values included in each of regions C1, C2, and C3 may be calculated using the images 200A, 200B, and 200C. For example, color coordinate values of the image 200C captured while light having a relatively high intensity is irradiated may have a relatively great x value and a relatively small y value as compared to color coordinate values of the images 200A and 200B. Thus, the controller 13 may increase an x value of a reference region compared to color coordinate values calculated using the respective images 200A, 200B, and 200C, and may decrease a y value of the reference region, when a level of optical power of the lighting unit 11 is high. Conversely, when the level of optical output of the lighting unit 11 is low, the controller 13 may decrease the x value of the reference region compared to the color coordinate values calculated using the respective images 200A, 200B, and 200C, and may increase the y value of the reference region, when the level of optical power of the lighting unit 11 is high.

For example, when the testing apparatus 10 simultaneously irradiates two or more light emitting device packages 200, disposed adjacent to each other, with light to obtain images, amounts of light received to the respective light emitting device packages 200 may be different according to locations of the respective light emitting device packages 200. The controller 13 may apply different reference regions to the light emitting device packages 200 the images of which have been obtained to separately determine whether the respective light emitting device packages 200 are defective.

Figure 12:
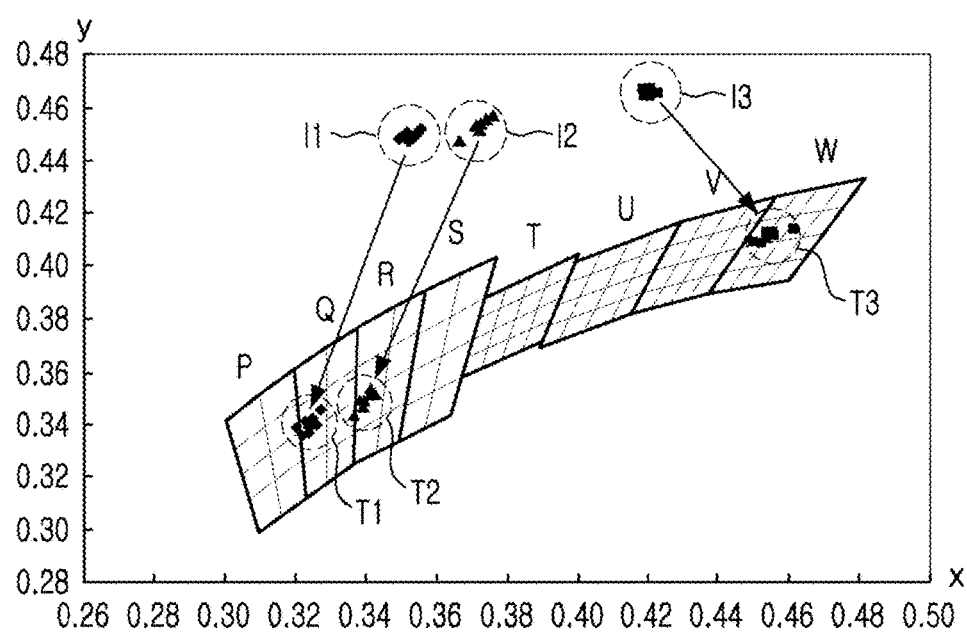
FIGS. 12 and 13 are graphs of color coordinate values calculated by a testing apparatus for testing a light emitting device package according to an example embodiment.
Figure 13:
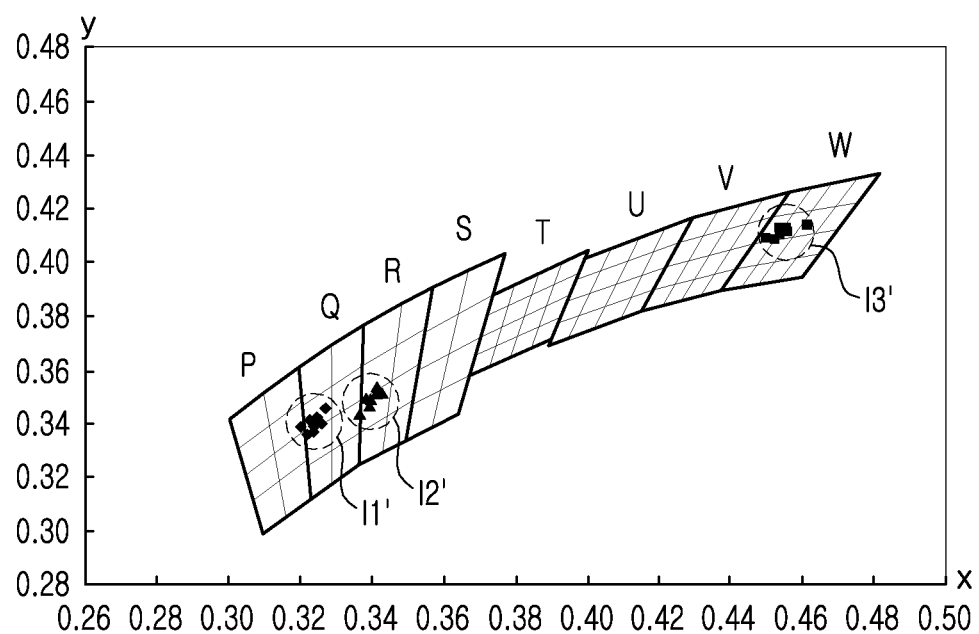

FIGS. 12 and 13 are graphs of color coordinate values calculated by a testing apparatus for testing a light emitting device package according to an example embodiment. The graphs will hereinafter be described with reference to FIG. 2.

First, color coordinate systems illustrated in FIGS. 12 and 13 may be Yxy color coordinate systems. Each of the Yxy color coordinate systems may be divided into a plurality of spaces P, Q, R, S, T, U, V, and W according to color temperatures. Referring first to the graph of FIG. 12, color coordinate values I1, I2, and I3 obtained by imaging the light emitting device packages 40 by the testing apparatus 10 according to an example embodiment, and color coordinate values T1, T2, and T3 measured by actually supplying power to the identical light emitting device packages 40 are illustrated. As illustrated in the graph of FIG. 12, the color coordinate values I1 to I3 obtained using the light emitting device packages 40 by the testing apparatus 10 according to an example embodiment may be different from the color coordinate values T1 to T3 measured by supplying power to the light emitting device packages 40. Thus, a process for compensating for a difference between the color coordinate values I1 to I3 and the color coordinate values T1 to T3 may be implemented.

In an example embodiment, the controller 13 may compensate for the difference with values similar to the color coordinate values T1 to T3 by multiplying each of x and y values of the color coordinate values I1 to I3, obtained using the images of the light emitting device packages 40, by a certain coefficient. The respective coefficients that the controller 13 reflects in the color coordinate values I1 to I3 may change according to the x and y values, and may be determined according to color temperatures of the spaces P to W including the color coordinate values I1 to I3, and to optical power of the lighting unit 11 that irradiates light when the images of the light emitting device packages 40 are captured. In an example embodiment, the coefficients for each of the spaces Q, R, and W may be as follows in Table 1. As illustrated in Table 1, compensated color coordinate values I1', I2', and I3' similar to the actual color coordinate values T1 to T3 may be calculated by compensating for the color coordinate values I1 to I3 obtained reflecting the certain coefficients and using the image, as illustrated in FIG. 13.

TABLE 1

| Section | Q | R | W |
| --- | --- | --- | --- |
| CIEx | $0.918X_{IQ} = X_{TQ}$ | $0.913X_{IR} = X_{TR}$ | $1.080X_{IW} = X_{TW}$ |
| CIEy | $0.757Y_{IQ} = Y_{TQ}$ | $0.770Y_{IR} = Y_{TR}$ | $0.880Y_{IW} = Y_{TW}$ |

FIGS. 14 through 19 are cross-sectional views of semiconductor light emitting devices that may be applied to a light emitting device package according to an example embodiment.

Figure 14:
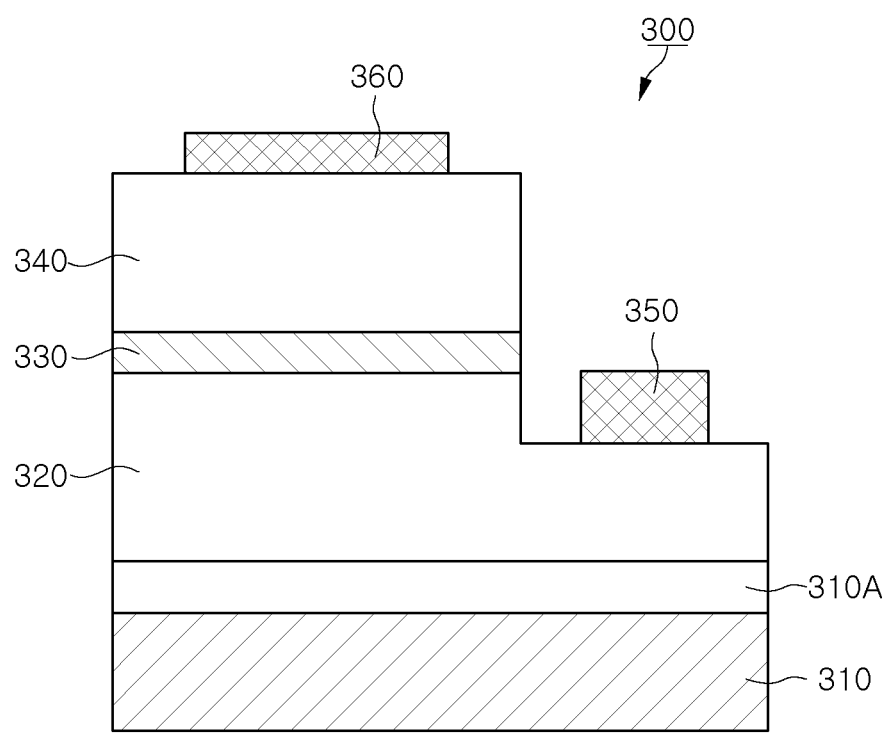
FIGS. 14, 15, 16, 17, 18, and 19 are cross-sectional views of semiconductor light emitting devices that may be applied to a light emitting device package according to an example embodiment.

Referring first to FIG. 14, a semiconductor light emitting device 300 according to an example embodiment may include a substrate 310, a first conductive semiconductor layer 320, an active layer 330, and a second conductive semiconductor layer 340. The first conductive semiconductor layer 320 may have a first electrode 350 formed thereon, and the second conductive semiconductor layer 340 may have a second electrode 360 formed thereon. The second electrode 360 and the second conductive semiconductor layer 340 may further have an ohmic contact layer selectively disposed in a space therebetween.

First, at least one of an insulating substrate, a conductive substrate, or a semiconductor substrate may be selected as the substrate 310 according to various example embodiments. The substrate 310 may be, for example, sapphire, silicon carbide (SiC), silicon (Si), $MgAl_2O_4$, MgO, $LiAlO_2$, $LiGaO_2$, or GaN. For epitaxial growth of a GaN material, the same kind of substrate, for example, a GaN substrate, may be selected as the substrate 310, and a sapphire substrate, a silicon carbide (SiC) substrate, or the like, may be mainly used as a different kind of substrate. When the different kind of substrate is used, a difference between lattice constants of a substrate material and a thin film material may cause a defect, such as a dislocation, to be increased, and a difference between thermal expansion coefficients of the substrate material and the thin film material may result in bending of the different kind of substrate when a temperature changes, and thus the bending may lead to cracking of a thin film. In order to address the above issues, the substrate 310, and the first conductive semiconductor layer 320 based on GaN may have a buffer layer 310A disposed therebetween.

When the first conductive semiconductor layer 320 including GaN is grown on a heterogeneous substrate, a mismatch between lattice constants of a substrate material and a thin film material may cause dislocation density to be increased, and a difference between thermal expansion coefficients of the substrate material and the thin film material may lead to cracking and bending of the heterogeneous substrate. In order to address the abovementioned dislocation and cracking, the substrate 310 and the first conductive semiconductor layer 320 may have the buffer layer 310A disposed therebetween. The buffer layer 310A may adjust the extent of bending of the substrate 310 when the active layer 330 is grown to reduce a wavelength distribution of a wafer.

The buffer layer 310A may be formed using $Al_xIn_yGa_{1-x-y}N$ ($0 \leq x \leq 1$, $0 \leq y \leq 1$), in particular, GaN, AlN, AlGaN, InGaN, or InGaNAlN, using another material, such as $ZrB_2$, $HfB_2$, ZrN, HfN, or TiN, or any combination thereof. The buffer layer 310A may also be formed by combining a plurality of layers or gradually changing compositions thereof.

Since there is a great difference between thermal expansion coefficients of a Si substrate and GaN, a GaN-based thin film is grown at high temperatures and then cooled at room temperature when the GaN-based thin film is grown on the Si substrate. In this case, the difference between the thermal expansion coefficients of the Si substrate and the GaN-based thin film may cause tensile stress to act on the GaN-based thin film, and thus cracking may easily occur. As a method of preventing cracking, use of a method of growing a thin film such that the thin film may be subject to compression stress during growth thereof may allow tensile stress to be compensated. A difference between lattice constants of silicon (Si) and GaN may be more likely to cause a defect. Because stress control for suppressing bending, as well as defect control in the case of use of an Si substrate need to be simultaneously performed, a buffer layer 310A having a complex structure may be used.

In order to form the buffer layer 310A, an AlN layer may first be formed on the substrate 310. A material not containing Ga may be used, and a material including SiC as well as AlN may also be used, in order to prevent a reaction between silicon (Si) and gallium (Ga). The AlN layer may be grown at a temperature between 400° C. to 1,300° C. using an aluminum (Al) source and a nitrogen (N) source, and AlGaN interlayers controlling stress on GaN between a plurality of AlN layers may be inserted in a space between the plurality of AlN layers.

The first and second conductive semiconductor layers 320 and 340 may include semiconductors doped with n-type and p-type impurities, respectively. The first and second conductive semiconductor layers 320 and 340 are not limited thereto, but may be p-type and n-type semiconductor layers, respectively. For example, each of the first and second conductive semiconductor layers 320 and 340 may include a group III nitride semiconductor layer, such as a material having a composition of $Al_xIn_yGa_{1-x-y}N$ ($0 \leq x \leq 1$, $0 \leq y \leq 1$, $0 \leq x+y \leq 1$). The present example embodiment is not limited thereto, and a material, such as an AlGaInP-based semiconductor or an AlGaAs-based semiconductor may be used.

Meanwhile, each of the first and second conductive semiconductor layers 320 and 340 may include a monolayer structure, and also may have a multilayer structure having different compositions or thicknesses. For example, each of the first and second conductive semiconductor layers 320 and 340 may include a carrier injection layer able to increase injection efficiency of electrons and holes, and may also include various forms of superlattice structures.

The first conductive semiconductor layer 320 may further include a current diffusion layer in a portion thereof adjacent to the active layer 330. The current diffusion layer may have a structure in which a plurality of layers having different compositions, $In_xAl_yGa_{(1-x-y)}N$, or different impurity contents are repeatedly stacked, or may have an insulating material layer partially formed thereon.

The second conductive semiconductor layer 340 may further include an electron blocking layer in a portion thereof adjacent to the active layer 330. The electron blocking layer may have a structure in which a plurality of layers having different compositions, $In_xAl_yGa_{(1-x-y)}N$, are stacked, or at least one layer having a composition of $Al_yGa_{(1-y)}N$, and may prevent electrons from moving to the second conductive semiconductor layer 340 due to having a band gap higher than that of the active layer 330.

In an example embodiment, the first and second conductive semiconductor layers 320 and 340 and the active layer 330 may be manufactured using a metal organic chemical vapor deposition (MOCVD) apparatus. In order to manufacture the first and second conductive semiconductor layers 320 and 340 and the active layer 330, organic metal compound gas (for example, trimethyl gallium (TMG), trimethyl aluminum (TMA), or the like) and nitrogen-containing gas (ammonia ($NH_3$) or the like) as reaction gases may be supplied to the inside of a reaction vessel in which the substrate 310 is installed. The substrate 310 may remain at a high temperature from 900° C. to 1100° C. Impurity gas may be supplied, for example, while a nitride gallium-based compound semiconductor is grown on the substrate 310. Thus, the nitride gallium-based compound semiconductor may be stacked in an undoped type, an n type, or a p type. Silicon (Si) has been well-known as an n-type impurity, and zinc (Zn), cadmium (Cd), beryllium (Be), magnesium (Mg), calcium (Ca), barium (Ba) or the like may be provided as a p-type impurity, and magnesium (Mg) or zinc (Zn) may be mainly used as a p-type impurity.

The active layer 330 disposed in a space between the first and second conductive semiconductor layers 320 and 340 may have a multiple quantum well (MQW) structure in which quantum well layers and quantum barrier layers are alternately stacked on each other. For example, in the case that the active layer 330 is a nitride semiconductor, the active layer 330 may have a GaN/InGaN structure, and may also have a single quantum well (SQW) structure. The first or second electrode 350 or 360 may contain a material, such as silver (Ag), nickel (Ni), aluminum (Al), rhodium (Rh), palladium (Pd), iridium (Ir), ruthenium (Ru), magnesium (Mg), zinc (Zn), platinum (Pt), or gold (Au). The semiconductor light emitting device 300 illustrated in FIG. 14 may have an epi-up structure, and may thus be connected to a circuit pattern included in a circuit board in a light emitting device package by a wire or the like.

Figure 15:
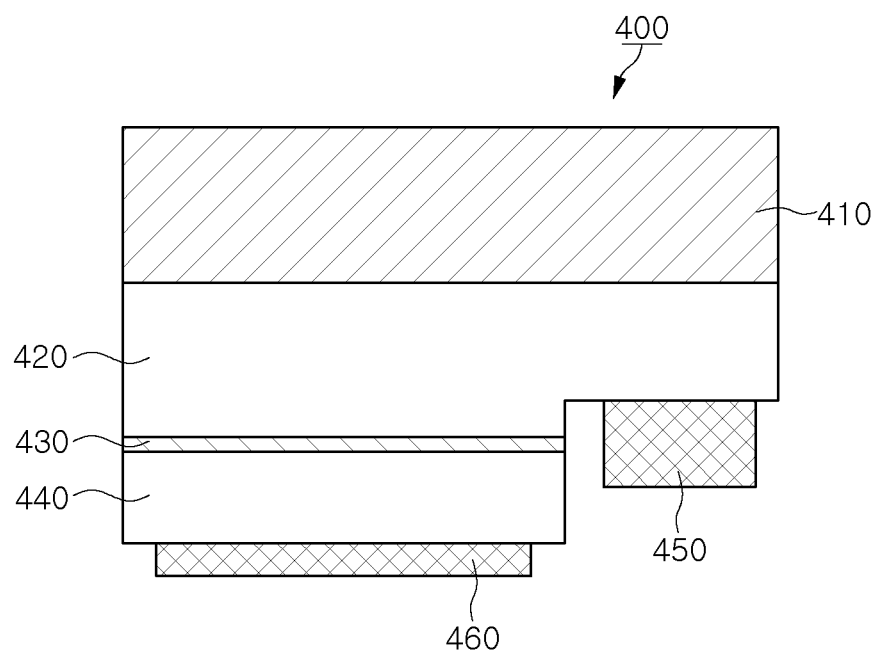

Referring to FIG. 15, a semiconductor light emitting device 400 according to an example embodiment may include a support substrate 410, a first conductive semiconductor layer 420, an active layer 430, a second conductive semiconductor layer 440, a first electrode 450, and a second electrode 460. The semiconductor light emitting device 400 according to an example embodiment illustrated in FIG. 15 may be bonded to a circuit board of a light emitting device package by a flip-chip bonding process. Since light generated by the active layer 430 needs to be transmitted to an upper portion thereof, the support substrate 410 may be formed of a material having light transmitting properties.

To reflect light traveling downwardly from the active layer 430, the second electrode 460 may be formed of a material having excellent electrical conductivity and reflectivity. As an example, the second electrode 460 may be formed of at least one of silver (Ag), nickel (Ni), aluminum (Al), rhodium (Rh), palladium (Pd), iridium (Ir), ruthenium (Ru), magnesium (Mg), zinc (Zn), platinum (Pt), and gold (Au).

Figure 16:
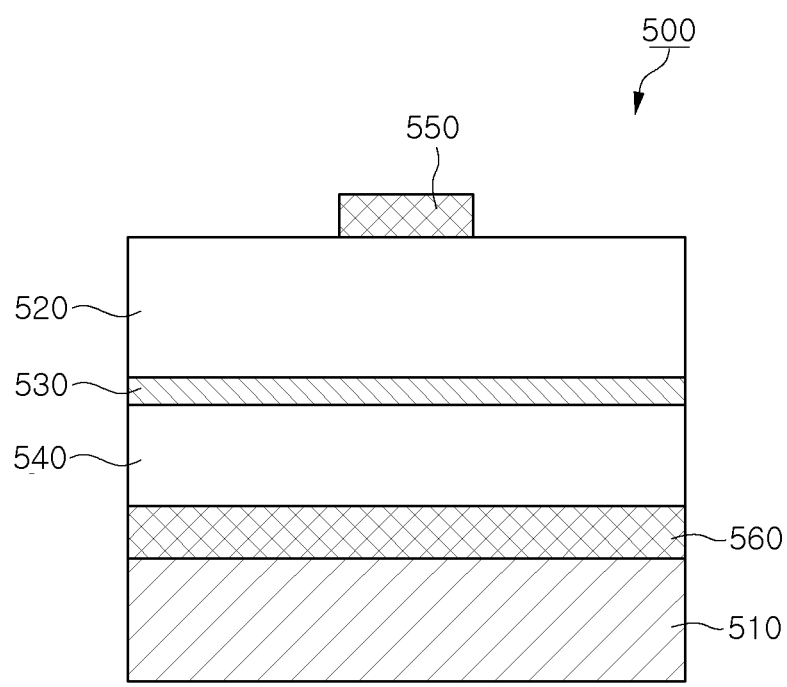

Referring to FIG. 16, a semiconductor light emitting device 500 according to an example embodiment is illustrated. The semiconductor light emitting device 500 according to the example embodiment illustrated in FIG. 16 may include a first conductive semiconductor layer 520, an active layer 530, a second conductive semiconductor layer 540, a first electrode 550 bonded to the first conductive semiconductor layer 520, and a second electrode 560 bonded to the second conductive semiconductor layer 560. The second electrode 560 may have a conductive substrate 510 disposed on a lower surface thereof, and the conductive substrate 510 may be directly mounted on a circuit board, or the like, configuring a light emitting device package. In the light emitting device package, the conductive substrate 510 may be directly mounted on the circuit board, and the first electrode 550 may be electrically connected to a circuit pattern of the circuit board by a wire or the like.

Similarly to the semiconductor light emitting devices 300 and 400 described above, the first and second conductive semiconductor layers 520 and 540 may include n-type and p-type nitride semiconductors, respectively. Meanwhile, the active layer 530 disposed in a space between the first and second conductive semiconductor layers 520 and 540 may have an MQW structure in which nitride semiconductor layers having different compositions are alternately stacked, and may selectively have an SQW structure.

The first electrode 550 may be disposed on an upper surface of the first conductive semiconductor layer 520, and the second electrode 560 may be disposed on a lower surface of the second conductive semiconductor layer 540. The active layer 530 of the semiconductor light emitting device 500 illustrated in FIG. 16 may allow light, generated by electron-hole recombination, to be transmitted to the upper surface of the first conductive semiconductor layer 520 on which the first electrode 550 is disposed. Thus, in order for light, generated by the active layer 530, to be reflected in a direction of the upper surface of the first conductive semiconductor layer 520, the second electrode 560 may be formed of a material having high reflectivity. The second electrode 560 may include at least one of silver (Ag), aluminum (Al), nickel (Ni), chromium (Cr), copper (Cu), gold (Au), palladium (Pd), platinum (Pt), tin (Sn), titanium (Ti), tungsten (W), rhodium (Rh), iridium (Ir), ruthenium (Ru), magnesium (Mg), and zinc (Zn), or alloys thereof.

Figure 17:
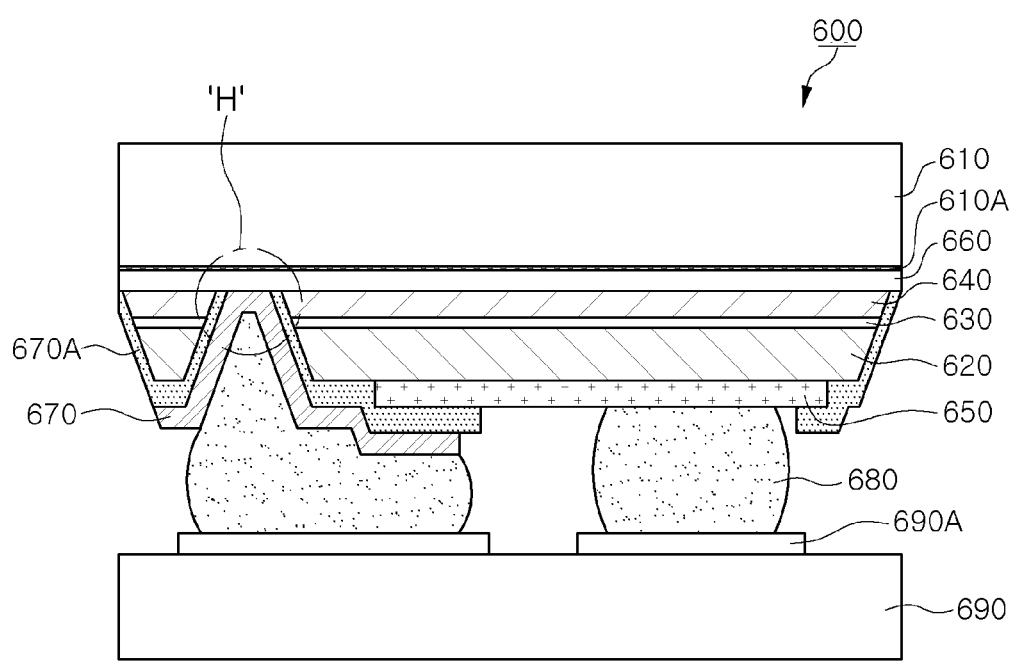

Referring to FIG. 17, a semiconductor light emitting device 600 according to an example embodiment may include a first conductive semiconductor layer 620, a second conductive semiconductor layer 640, an active layer 630 positioned therebetween, and a first electrode 650 and a second electrode 660 respectively connected to the first conductive semiconductor layer 620 and the second conductive semiconductor layer 640. In an example embodiment, the first and second electrodes 650 and 660 may be respectively disposed on opposite surfaces of the first and second conductive semiconductor layers 620 and 640 with the first conductive semiconductor layer 620, the active layer 630, and the second conductive semiconductor layer 640 interposed therebetween. The second electrode 660 may have a support substrate 610 bonded thereto by a bonding layer 610A to support the semiconductor light emitting device 600.

The light emitting device 600 according to an example embodiment may further include a connecting electrode 670 as an electrode element related to the second electrode 660. The connecting electrode 670 may be connected to the second electrode 660 by a through hole H formed by removing at least regions of the first and second conductive semiconductor layers 620 and 640 and the active layer 630. The through hole H may allow at least a region of the second electrode 660 to be exposed, and the second electrode 660 and the connecting electrode 670 may be connected to each other in the exposed region. The connecting electrode 670 may be formed along side walls of the through hole H. An insulating layer 670A may be disposed in a space between the connecting electrode 670 and the side walls of the through hole H to prevent the connecting electrode 670, the active layer 630, and the first conductive semiconductor layer 620 from being electrically connected to each other.

The abovementioned electrode structure may be applied more efficiently when the first and second conductive semiconductor layers 620 and 640 are n-type and p-type nitride semiconductor layers, respectively. The p-type nitride semiconductor layer may have a level of contact resistance higher than that of contact resistance of the n-type nitride semiconductor layer, and obtaining ohmic contact may thus be difficult. However, in the example embodiment illustrated in FIG. 17, the second electrode 660 may be disposed over the entirety of a surface of the support substrate 610 to secure a sufficient contact region between the second conductive semiconductor layer 640 and the second electrode 660, thus obtaining ohmic contact with the p-type nitride semiconductor layer.

Meanwhile, the semiconductor light emitting device 600 according to the example embodiment illustrated in FIG. 17 may have a flip-chip structure in which light may be emitted in a direction of the support substrate 610. For example, the first electrode 650 and the connecting electrode 670 may be electrically connected to a circuit pattern 690A of a circuit board 690 through a solder bump 680 or the like. Thus, the first electrode 650 may include an electrode material having high reflectivity, as well as ohmic contact characteristics. Each of the second electrode 660 and the support substrate 610 may have a high degree of light transmitting properties. For example, the first electrode 650 may include a material, such as silver (Ag), nickel (Ni), aluminum (Al), rhodium (Rh), palladium (Pd), iridium (Ir), ruthenium (Ru), magnesium (Mg), zinc (Zn), platinum (Pt), or gold (Au). The second electrode 660 may be a light transmitting metal, such as nickel (Ni)/gold (Au), or a transparent conductive oxide or nitride, such as an indium tin oxide (ITO). The support substrate 610 may be a glass substrate, or a substrate formed of a light transmitting polymer resin.

The connecting electrode 670 may be electrically insulated from the first conductive semiconductor layer 620 and the active layer 630 by the insulating layer 670A. As illustrated in FIG. 17, the insulating layer 670A may be formed along the side walls of the through hole H. The insulating layer 670A may also be formed on side surfaces of the first and second conductive semiconductor layers 620 and 640 and the active layer 630 as a passivation layer for the light emitting device 600. The insulating layer 670A may include a silicon oxide or a silicon nitride.

Figure 18:
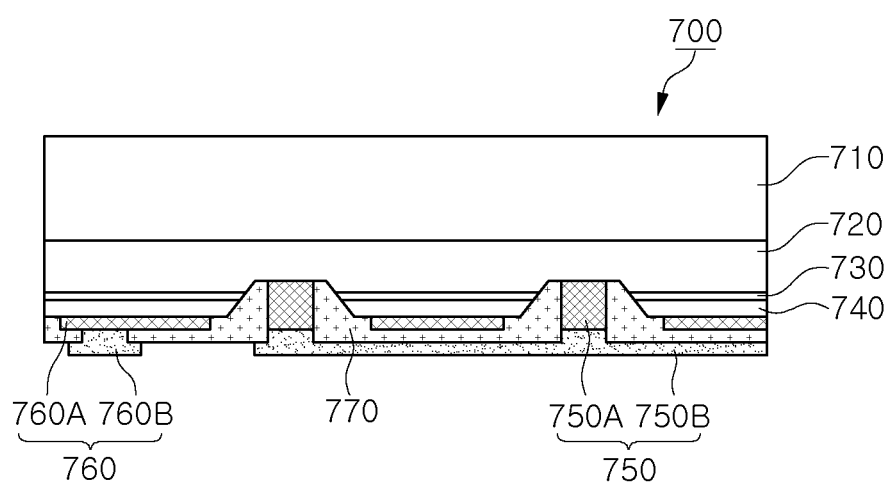

Referring to FIG. 18, a semiconductor light emitting device 700 according to an example embodiment is disclosed. The semiconductor light emitting device 700 may include a first conductive semiconductor layer 720, an active layer 730, and a second conductive semiconductor layer 740 sequentially stacked on a surface of a substrate 710, a first electrode 750, and a second electrode 760. The semiconductor light emitting device 700 may also include insulators 770. The first electrode 750 and the second electrode 760 may include a first contact electrode 750A and a second contact electrode 760A, and a first connecting electrode 750B and a second connecting electrode 760B, respectively, and regions of the first and second contact electrodes 750A and 760A exposed by the insulators 770 may be connected to the first and second connecting electrodes 750B and 760B.

The first contact electrode 750A may be provided as a conductive via passing through the second conductive semiconductor layer 740 and the active layer 730 to be connected to the first conductive semiconductor layer 720. The second contact electrode 760A may be connected to the second conductive semiconductor layer 740. The conductive via may be provided as a plurality of conductive vias in a single light emitting device region.

The first and second contact electrodes 750A and 760A may be formed by depositing conductive ohmic materials on the first and second conductive semiconductor layers 720 and 740. Each of the first and second contact electrodes 750A and 760A may include at least one of silver (Ag), aluminum (Al), nickel (Ni), chromium (Cr), copper (Cu), gold (Au), palladium (Pd), platinum (Pt), tin (Sn), titanium (Ti), tungsten (W), rhodium (Rh), iridium (Ir), ruthenium (Ru), magnesium (Mg), zinc (Zn), or alloys thereof. The second contact electrode 760A may function to reflect light generated by the active layer 730 and then transmitted to a lower portion of the semiconductor light emitting device 700.

The insulators 770 may have open regions exposing at least portions of the first and second contact electrodes 750A and 760A, and the first and second connecting electrodes 750B and 760B may be connected to the first and second contact electrodes 750A and 760A, respectively. The insulators 770 may be deposited to have a thickness from 0.01 μm to 3 μm at a temperature of 500° C. or below by an $SiO_2$ or SiN chemical vapor deposition (CVD) process. The first and second electrodes 750 and 760 may be mounted on a light emitting device package in a flip chip form.

The first and second electrodes 750 and 760 may be electrically isolated from each other by the insulators 770. The insulators 770 may be any material having electrically insulating characteristics, and, for example, may be a material having low light absorption to prevent light extraction efficiency of the semiconductor light emitting device 700 from deteriorating. For example, a silicon oxide, such as $SiO_2$, and a silicon nitride, such as $SiO_xN_y$ or $Si_xN_y$, may be used. For example, a light-reflective structure may be formed by dispersing a light-reflective filler in a light transmitting material.

The substrate 710 may have a first surface and a second surface opposing each other, and at least one of the first and second surfaces may also have an uneven structure formed thereon. An unevenness structure that may be formed on a surface of the substrate 710 may be constructed by etching a portion of the substrate 710, and may include the same material as the substrate 710, or may include a heterogeneous material different from the substrate 710. For example, an uneven structure may be formed at an interface between the substrate 710 and the first conductive semiconductor layer 720 to allow a path of light, emitted by the active layer 730, to vary, so that a light absorption rate of a semiconductor layer may be reduced, and a light scattering ratio may be increased, thus increasing light extraction efficiency. The substrate 710 and the first conductive semiconductor layer 720 may have a buffer layer disposed therebetween.

Figure 19:
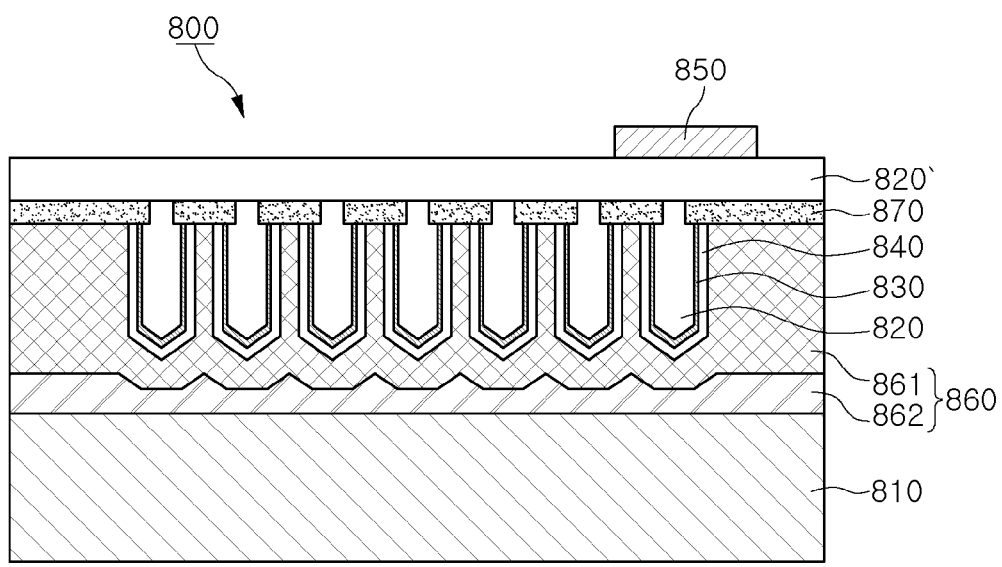
Figure 20:
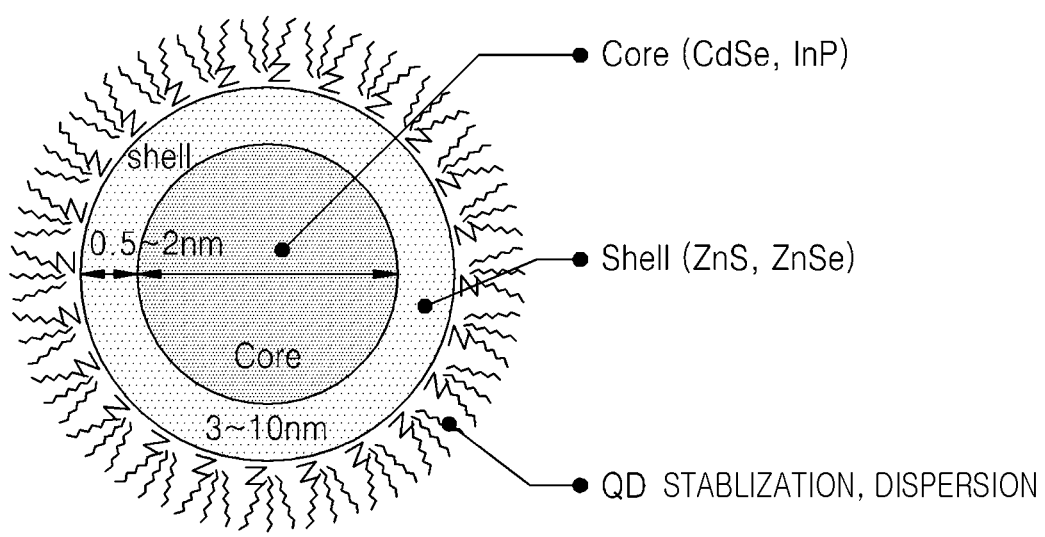
FIG. 20 is a diagram of a light conversion material that may be contained in a light transmitting resin of a light emitting device package according to an example embodiment.

Referring to FIG. 19, a semiconductor light emitting device 800 according to an example embodiment may have a light emitting nanostructure. The semiconductor light emitting device 800 may include a base layer 820' including a first conductive semiconductor material, a mask layer 870 provided on the base layer 820' and having a plurality of openings, and nanocores 820 formed in the openings of the mask layer 870. Each of the nanocores 820 may have an active layer 830 and a second conductive semiconductor layer 840 provided thereon. The nanocores 820, the active layer 830, and the second conductive semiconductor layer 840 may form the light emitting nanostructure.

The second conductive semiconductor layer 840 may have a second contact electrode 861 provided thereon, and the second contact electrode 861 may have a second connecting electrode 862 provided on a surface thereof. The second contact electrode 861 and the second connecting electrode 862 may be provided as a second electrode 860. The second electrode 860 may have a support substrate 810 bonded to a surface thereof, and the support substrate 810 may be a conductive substrate or an insulating substrate. When the support substrate 810 is conductive, the support substrate 810 may be directly mounted on a circuit board of a light emitting device package. The base layer 820' including the first conductive semiconductor material may have a first electrode 850 provided thereon. The first electrode 850 may be connected to a circuit pattern included in the circuit board of the light emitting device package by a wire or the like.

FIG. 22 is a diagram of a light conversion material that may be contained in a light transmitting resin of a light emitting device package according to an example embodiment.

A wavelength conversion material may convert a wavelength of light emitted by a light emitting device, and may be various types of materials, such as a phosphor and a quantum dot (QD).

As an example, a phosphor applied to a wavelength conversion material may have the following formulae and colors: yellow and green $Y_3Al_5O_{12}$:Ce, yellow and green $Tb_3Al_5O_{12}$:Ce, and yellow and green $Lu_3Al_5O_{12}$:Ce (oxide-based); yellow and green $(Ba,Sr)_2SiO_4$:Eu and yellow and orange $(Ba,Sr)_3SiO_5$:Ce (silicate-based); green β-SiAlON: Eu, yellow $La_3Si_6N_{11}$:Ce, orange α-SiAlON:Eu, red $CaAlSiN_3$:Eu, red $Sr_2Si_5N_8$:Eu, red $SrSiAl_4N_7$:Eu, red $SrLiAl_3N_4$:Eu, and red $Ln_{4-x}(Eu_zM_{1-z})_xSi_{12-y}Al_yO_{3+x+y}N_{18-x-y}$ (0.5≤x≤3, 0<z<0.3, 0<y≤4) (nitride-based)-Formula (1), in which Ln may be at least one kind of element selected from the group consisting of group IIIa elements and rare earth elements, and M may be at least one kind of element selected from the group consisting of calcium (Ca), barium (Ba), strontium (Sr), and magnesium (Mg); and KSF-based red $K_2SiF_6$:$Mn_4^+$, KSF-based red $K_2TiF_6$:$Mn_4^+$, KSF-based red $NaYF_4$:$Mn_4^+$, KSF-based red $NaGdF_4$:$Mn_4^+$, and KSF-based red $K_3SiF_7$:$Mn^{4+}$ (fluoride-based).

A phosphor composition may be required to conform with stoichiometry, and respective elements thereof may be replaced with other elements in each group in which a corresponding element is included on the periodic table. For example, strontium (Sr) may be substituted with barium (Ba), calcium (Ca), magnesium (Mg), or the like, of alkaline earth metals (group II), and yttrium (Y) may be substituted with terbium (Tb), lutetium (Lu), scandium (Sc), gadolinium (Gd), or the like, of lanthanides. For example, europium (Eu), an activator, or the like, may be substituted with cerium (Ce), terbium (Tb), praseodymium (Pr), erbium (Er), ytterbium (Yb), or the like, according to desired energy levels. An activator may be applied alone, or an additional sub-activator, or the like, may be applied to modify characteristics.

In particular, a fluoride-based red phosphor may be coated with a fluoride not containing manganese (Mn), or may further include an organic coating on a surface of the fluoride-based red phosphor or on a surface of the fluoride-based red phosphor coated with a fluoride not containing manganese (Mn) to improve reliability at high temperatures and high humidity. Differently from other phosphors, the fluoride-based red phosphor may realize a narrow full width at half maximum (FWHM) equal to or less than 40 nm, and may thus be utilized in a high-resolution television, such as an ultra-high definition (UHD) television.

Table 2 below indicates types of phosphors by application fields of a light emitting device package using a blue LED chip (dominant wavelength: 440 nm to 460 nm) or an UV LED chip (dominant wavelength: 380 nm to 430 nm).

TABLE 2

| Use | Phosphor |
|---|---|
| LED TV BLU | $\beta$-SiAlON:Eu$^{2+}$, (Ca, Sr)AlSiN$_3$:Eu$^{2+}$, La$_3$Si$_6$N$_{11}$:Ce$^{3+}$, K$_2$SiF$_6$:Mn$^{4+}$, SrLiAl$_3$N$_4$:Eu, Ln$_{4-x}$(Eu$_z$M$_{1-z}$)$_x$Si$_{12-y}$Al$_y$O$_{3+x+y}$N$_{18-x-y}$ ($0.5 \leq x \leq 3$, $0 < z < 0.3$, $0 < y \leq 4$), K$_2$TiF$_6$:Mn$^{4+}$, NaYF$_4$:Mn$^{4+}$, NaGdF$_4$:Mn$^{4+}$, K$_3$SiF$_7$:Mn$^{4+}$ |
| Lighting Device | Lu$_3$Al$_5$O$_{12}$:Ce$^{3+}$, Ca-$\alpha$-SiAlON:Eu$^{2+}$, La$_3$Si$_6$N$_{11}$:Ce$^{3+}$, (Ca, Sr)AlSiN$_3$:Eu$^{2+}$, Y$_3$Al$_5$O$_{12}$:Ce$^{3+}$, K$_2$SiF$_6$:Mn$^{4+}$, SrLiAl$_3$N$_4$:Eu, Ln$_{4-x}$(Eu$_z$M$_{1-z}$)$_x$Si$_{12-y}$Al$_y$O$_{3+x+y}$N$_{18-x-y}$($0.5 \leq x \leq 3$, $0 < z < 0.3$, $0 < y \leq 4$), K$_2$TiF$_6$:Mn$^{4+}$, NaYF$_4$:Mn$^{4+}$, NaGdF$_4$:Mn$^{4+}$, K$_3$SiF$_7$:Mn$^{4+}$ |
| Side Viewing Screen (Mobile Device, Laptop PC, etc.) | Lu$_3$Al$_5$O$_{12}$:Ce$^{3+}$, Ca-$\alpha$-SiAlON:Eu$^{2+}$, La$_3$Si$_6$N$_{11}$:Ce$^{3+}$, (Ca, Sr)AlSiN$_3$:Eu$^{2+}$, Y$_3$Al$_5$O$_{12}$:Ce$^{3+}$, (Sr, Ba, Ca, Mg)$_2$SiO$_4$:Eu$^{2+}$, K$_2$SiF$_6$:Mn$^{4+}$, SrLiAl$_3$N$_4$:Eu, Ln$_{4-x}$(Eu$_z$M$_{1-z}$)$_x$Si$_{12-y}$Al$_y$O$_{3+x+y}$N$_{18-x-y}$ ($0.5 \leq x \leq 3$, $0 < z < 0.3$, $0 < y \leq 4$), K$_2$TiF$_6$:Mn$^{4+}$, NaYF$_4$:Mn$^{4+}$, NaGdF$_4$:Mn$^{4+}$, K$_3$SiF$_7$:Mn$^{4+}$ |
| Electronic Lighting Device (Headlamp, etc.) | Lu$_3$Al$_5$O$_{12}$:Ce$^{3+}$, Ca-$\alpha$-SiAlON:Eu$^{2+}$, La$_3$Si$_6$N$_{11}$:Ce$^{3+}$, (Ca, Sr)AlSiN$_3$:Eu$^{2+}$, Y$_3$Al$_5$O$_{12}$:Ce$^{3+}$, K$_2$SiF$_6$:Mn$^{4+}$, SrLiAl$_3$N$_4$:Eu, Ln$_{4-x}$(Eu$_z$M$_{1-z}$)$_x$Si$_{12-y}$Al$_y$O$_{3+x+y}$N$_{18-x-y}$($0.5 \leq x \leq 3$, $0 < z < 0.3$, $0 < y \leq 4$), K$_2$TiF$_6$:Mn$^{4+}$, NaYF$_4$:Mn$^{4+}$, NaGdF$_4$:Mn$^{4+}$, K$_3$SiF$_7$:Mn$^{4+}$ |

For example, quantum dots (QDs) may be used as wavelength conversion materials. Here, the QDs may replace phosphors, or may be mixed with phosphors.

FIG. 22 is a cross-sectional view of a QD. The QD may have a core-shell structure using a group III-V compound semiconductor or a group II-VI compound semiconductor. For example, the QD may have a core, such as CdSe or InP, and a shell, such as ZnS or ZnSe. The QD may also include a ligand stabilizing the core and the shell. For example, a diameter of the core may range from 1 nm to 30 nm, and as an example, may range from 3 nm to 10 nm. A thickness of the shell may range from 0.1 nm to 20 nm, and as an example, may range from 0.5 nm to 2 nm.

The QD may implement various colors according to sizes thereof, and in particular, when used as a phosphor substitute, may be employed as a red or green phosphor. When the QD is used, a narrow FWHM (for example, about 35 nm) may be implemented.

A wavelength conversion material may be provided to be contained in an encapsulant, or may also be previously manufactured in a film form so as to be bonded to a surface of an optical device, such as an LED chip or a light guide plate. When the wavelength conversion material previously manufactured in the film form is used, a wavelength conversion material having a uniform thickness may be easily implemented.

According to an example embodiment, an apparatus is provided, which may test whether the amount of resin sprayed by dispensers is proper without an expensive device, for example, a CIE detector or the like.

As set forth above, according to example embodiments, a testing apparatus and a manufacturing apparatus for manufacturing a light emitting device package may irradiate a light emitting device package having a light transmitting resin containing a light conversion material with light having a certain color to obtain an image of the light emitting device package onto which resin containing a light conversion material is sprayed, and may calculate color coordinates of the light emitting device package using the obtained image to determine whether a proper amount of the light transmitting resin is included in the light emitting device package according to whether the calculated color coordinates are outside of a certain reference region. The reference area may include color coordinates calculated using light emitted by the light emitting device package in the case that a proper amount of resin is dispensed. Thus, whether a dispensed amount of lighting transmitting resin and a content of a light conversion material included in the light transmitting resin are sufficient may be efficiently determined without a high-priced device.

While example embodiments have been shown and described above, it will be apparent to those skilled in the art that modifications and variations could be made without departing from the scope of the present inventive concept as defined by the appended claims.

What is claimed is:

1. An apparatus comprising:
    a light source configured to radiate a light emitting device package including a light transmitting resin containing a light conversion material with light having a certain color, the light emitting device package further including a light emitting element;
    a camera configured to capture an image of the light emitting device package from a position above the light transmitting resin; and
    a controller configured to determine color coordinates of the light emitting device package based on the image, and determine whether the light emitting device package is defective based on the determined color coordinates, wherein the light emitting element is configured to emit light of a same color as the certain color.

2. The apparatus of claim 1, wherein the controller is further configured to set a reference region in a color coordinate system, wherein the reference region defines reference color coordinates, and determine whether the light emitting device package is defective based on a positional relationship between the determined color coordinates and the reference color coordinates, in the color coordinate system.

3. The apparatus of claim 2, wherein the controller is further configured to determine that the light emitting device package is defective in response to the determined color coordinates being outside of the reference region.

4. The apparatus of claim 3, wherein the controller is further configured to determine that an amount of the light conversion material contained in the light transmitting resin is excessive in response to the determined color coordinates being greater than upper limit values defining the reference color coordinates, in the color coordinate system.

5. The apparatus of claim 3, wherein the controller is further configured to determine that an amount of the light conversion material contained in the light transmitting resin is insufficient in response to the determined color coordinates being lower than lower limit values defining the reference color coordinates, in the color coordinate system.

6. The apparatus of claim 2, wherein the controller is further configured to set the reference region based on an optical output of the light source.

7. The apparatus of claim 1, wherein the controller is further configured to set a test region in the image, and determine the color coordinates of the light emitting device package based on red, green, and blue (RGB) values of pixels included in the test region.

8. The apparatus of claim 7, wherein the controller is further configured to determine an average of the RGB values of pixels included in the test region, and calculate the color coordinates of the light emitting device package based on the average.

9. The apparatus of claim 1, wherein the light source is further configured to radiate the light having the certain color to excite the light conversion material to emit light while the light emitting element is in an off state, and the controller is further configured to determine the color coordinates of the light emitting device package from the image based on optical characteristics of the light emitted by the light conversion material.

10. An apparatus comprising:
a resin dispenser configured to dispense a light transmitting resin containing a light conversion material onto a light emitting device package in dot units, the light emitting device package including a light emitting element; and
a controller coupled to a camera and configured to:
control the camera to radiate the light emitting device package, onto which the light transmitting resin has been dispensed, with light having a certain color, and to capture an image of the light emitting device package,
determine color coordinates based on a color coordinate system using the image captured by the camera, and
compare a reference region, defined in the color coordinate system, to the determined color coordinates to determine whether a dispensed amount of the light transmitting resin is defective, wherein the light emitting element is configured to emit light of a same color as the certain color.

11. The apparatus of claim 10, wherein the resin dispenser is further configured to dot the light emitting device package with the light transmitting resin.

12. The apparatus of claim 11, wherein the controller is further configured to determine that a dotting height of the light transmitting resin is defective in response to the determined color coordinates being outside of the reference region.

13. The apparatus of claim 12, wherein the controller is further configured to determine that the dotting height of the light transmitting resin is excessive in response to the determined color coordinates being greater than upper limit values of reference color coordinates of the reference region in the color coordinate system.

14. The apparatus of claim 12, wherein the controller is further configured to determine that the dotting height of the light transmitting resin is insufficient in response to the determined color coordinates being lower than lower limit values of reference color coordinates of the reference region in the color coordinate system.

15. The apparatus of claim 10, further comprising:
a jig configured to house a plurality of light emitting device packages, which includes the light emitting device package, the plurality of light emitting device packages being disposed on the jig in a plurality of rows and a plurality of columns,
wherein the camera is configured to simultaneously capture a first image of a first light emitting device package and a second image of a second light emitting device package disposed on the jig adjacent to each other, among the plurality of light emitting device packages.

16. The apparatus of claim 15, wherein the camera is further configured to determine first color coordinates and second color coordinates corresponding to the first light emitting device package and the second light emitting device package, respectively, based on the first image of the first light emitting device package and the second image of the second light emitting device package, and compare the first color coordinates and the second color coordinates to a first reference region and a second reference region different from the first reference region, and the first reference region and the second reference region are set in the color coordinate system.

17. An apparatus comprising:
a light source configured to emit light of a certain color onto a light emitting diode (LED) disposed in a cavity of a light emitting device package, the cavity being filled with a resin containing a light conversion material;
a camera configured to capture an image of a top of the resin disposed on the LED; and
a processor configured to determine color coordinates of the light conversion material dispersed in the resin from the image, and determine whether the light emitting device package is defective based on the determined color coordinates,
wherein the LED is configured to emit light of a same color as the certain color.

18. The apparatus of claim 17, wherein the processor is further configured to set a reference region in a color coordinate system, wherein the reference region defines reference color coordinates, and determine that the light emitting device package is defective in response to the determined color coordinates being disposed outside of the reference region, in the color coordinate system.

19. The apparatus of claim 18, wherein the processor is further configured to determine that an amount of the light conversion material contained in the resin or a height of the resin with respect to a top surface of the LED is excessive in response to values of the determined color coordinates being greater than upper limit values defining the reference color coordinates of the reference region in the color coordinate system.

20. The apparatus of claim 18, wherein the processor is further configured to determine that an amount of the light conversion material contained in the resin or a height of the resin with respect to a top surface of the LED is insufficient in response to values of the determined color coordinates being less than lower limit values defining the reference color coordinates of the reference region in the color coordinate system.

21. The apparatus of claim 18, wherein the processor is further configured to determine the reference region as corresponding to a target range of color coordinates of the light emitting device package when an amount of the light conversion material contained in the resin and a height of the resin with respect to a top surface of the LED are equal to certain reference values for generating a light of a desired color.

* * * * *